United States Patent [19]

Eisenbrand et al.

[11] Patent Number: 4,609,496
[45] Date of Patent: Sep. 2, 1986

[54] STEROID ESTERS OF N-(2-HALOGENOETHYL)-N-NITROSO-CARBAMOYL-AMINO ACIDS AND PEPTIDES THEREOF, AS WELL AS METHODS FOR PREPARING THEM

[75] Inventors: Gerhard Eisenbrand, Sandhausen; Joachim Schreiber, Heidelberg, both of Fed. Rep. of Germany

[73] Assignee: Stiftung Deutsches Krebsforshungszentrum, Heidelberg, Fed. Rep. of Germany

[21] Appl. No.: 557,138

[22] PCT Filed: Mar. 23, 1983

[86] PCT No.: PCT/EP83/00090

§ 371 Date: Nov. 17, 1983

§ 102(e) Date: Nov. 17, 1983

[87] PCT Pub. No.: WO83/03414

PCT Pub. Date: Oct. 13, 1983

[30] Foreign Application Priority Data

Mar. 23, 1982 [DE] Fed. Rep. of Germany ....... 3210637

[51] Int. Cl.$^4$ ................................................ C07J 1/00
[52] U.S. Cl. ............................. 260/397.4; 260/397.45; 260/397.47; 260/397.5; 260/998.2; 530/331; 530/330; 530/329
[58] Field of Search .................... 424/177; 260/397.45, 260/112.5, 397.4; 514/72

[56] References Cited

U.S. PATENT DOCUMENTS

4,177,269 12/1979 Fex et al. ................... 260/239.5
4,181,669 1/1980 Hansen et al. ................. 260/397.45

FOREIGN PATENT DOCUMENTS

2260261 2/1979 France ...................... 260/397.45
2028336 3/1980 United Kingdom ........... 260/397.45

OTHER PUBLICATIONS

Journal of Medicinal Chemistry (1972) vol. 15, No. 11, pp. 1158-1161.
Journal of Medicinal Chemistry, 1979, vol. 22, No. 2, pp. 200-202, "Synthesis of Steroidal nitrosoureas with Antitumor Activity" Hing-Yat P. Lam et al.
Chemical Abstract #96:69391C, "Synthesis of Potentially Antineoplastic Derivatives of N-[N-(2-Chloroethyl)-N-nitrosocarbamoyl]Amino Acids," Tang et al.

Primary Examiner—Elbert L. Roberts
Attorney, Agent, or Firm—Browdy & Neimark

[57] ABSTRACT

Steroid-N-(2-halogen ethyl)-N-nitroso-carbamoyl-amino acid or peptide esters of the general formula:

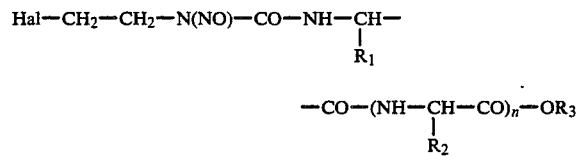

where $R_1$ and $R_2$, which may be identical or different, mean the radical of an amino acid beyond the C atom in the beta position (if present), $R_3$ means the radical of a steroid or a stilbene derivative pharmacologically similar in action, n is a number from 0-5 and Hal stands for chlorine or fluorine, as well as the method for preparing them by the conversion of an appropriate carbamoyl-amino acid or carbamoyl-peptide in a manner known per se with steroid alcohols or the conversion of steroid-amino acid or steroid-peptide esters with corresponding N-nitroso-carbamoylation or corresponding N-nitroso-carbamoyl-amino acids or peptides in a manner known per se.

15 Claims, No Drawings

STEROID ESTERS OF N-(2-HALOGENOETHYL)-N-NITROSO-CARBAMOYL-AMINO ACIDS AND PEPTIDES THEREOF, AS WELL AS METHODS FOR PREPARING THEM

DESCRIPTION

N-(2-ethyl chloride)-N-nitrosoureas ("CNU"), such as 1,3-bis-(2-ethyl chloride)-1-nitrosourea (BCNU), 1-(2-ethyl chloride)-3-cyclohexyl-1-nitrosourea (CCNU) and 1-(2-ethyl chloride)-3-(4-methyl)cyclohexyl-1-nitrosourea (MeCCNU) are important antineoplastic chemotherapeutic agents, from the clinical standpoint as well. (*Nitrosoureas in Cancer Treatment*, B. Serrou, P. S. Schein and J.-L. Imbach, editors, Elsevier/North-Holland Biomedicals Press, 1981; *Nitrosoureas: current status and new developments*, Academic Press, New York, 1981).

Along with their therapeutic efficacy, however, these substances also have a long-lasting cumulative toxicity (Eisenbrand et al., in: *Nitrosoureas in Cancer Treatment*, Elsevier 1981).

In order to obtain substances having a better therapeutic index, nitrosoureas have lately been synthesized with various substitutions (for instance, sugar, peptides, DNA bases) and experimentally tested.

It has been found that a series of tumors contain hormone receptors or are hormone-dependent. The attempt has already been made several times to improve the chemotherapy of such tumors by chemically bonding alkylanes, for example, to hormones in order to exploit the receptor affinity of the hormones for attaining target-specific transporting of the cytostatic alkylane into the tumor tissue. Some examples of substances of this type are Prednimustin ®, an ester of prednisolone and the alkylane chlorambucil (a phenylbutyric acid-mechlorethamine hydrochloride derivative), or Estracyt ®, an N,N-bis(2-ethyl chloride)-3-carbamate of the estradiol-17-β-phosphate. (*Cancer Chemotherapy*, edited by H. M. Pinedo, Excerpta Medica, Amsterdam-Oxford, 1979 and 1980.)

In contrast to these directly alkylating mechlorethamine hydrochloride derivatives, the present case relates to 2-halogen-alkylnitrosourea derivatives, which release a cross-linking alkylane only upon their decomposition in vivo. The CNU grouping must therefore be evaluated differently in both chemical and biological terms from the mechlorethamine hydrochloride grouping. As a rule, the CNU derivatives have a wider therapeutic range than the mechlorethamine hydrochloride derivatives. In the compounds described herein, a steroid molecule or a stilbene derivative acting pharmacologically similarly is bonded via an ester bond with an N-(2-halogen ethyl)-N-nitroso-carbamoyl-amino acid or with a peptide chain, the terminal amino acids of which carry the N-(2-halogen ethyl)-N-nitroso-carbamoyl group. The term "steroid" here also encompasses pharmacologically similarly acting stilbene derivatives having at least one OH group without steric hindrance. The steroids are preferably of the estrane, androstane or pregnane series, or corticosteroids. The OH groups used for the purpose of esterification are preferably located in positions 3, 6, 7, 15, 16, 17 and 21 of the pregnane structure. Additionally present OH groups may be free or else etherified (for instance, with methyl or ethyl) or esterified (for instance, with acetate or propenate).

The stilbene derivatives are preferably those having the following structures:

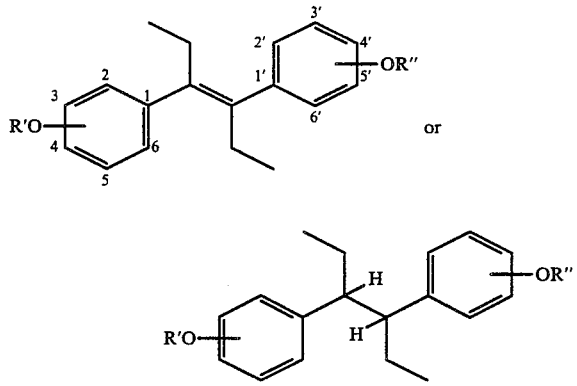

with R' =

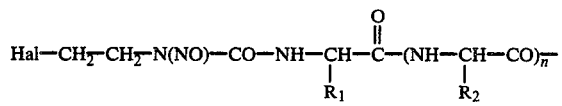

R' is accordingly the radical for supplementing the ethyl chloride nitrosourea, with $R_1$ and $R_2$ retaining their meaning given above; that is, they are radicals of amino acids. R"=H or R' or a low alkyl, in particular methyl or ethyl or acyl, in particular acetyl or benzoyl. The OR' or OR" substitutions are located at identical or different positions on the benzene rings, in particular in positions 3,3'; 4,4' and 3,4'. The ethylene double bond of the stilbene body may also be hydrogenated, as is evident from the formulas above.

To prepare these compounds, a CNU amino acid, a CNU di-, tri- or oligopeptide (up to hexapeptide), synthesized in accordance with W. Tang, G. Eisenbrand, Arch. Pharm. 314, 910–917 (1981) and with German Patent Application No. P 31 34 923.4, is put into an activated form, such as the imidazolide or a mixed acid anhydride (such as the paratoluolsulfonic acid) and converted with a steroid alcohol, which carries at least one OH group without steric hindrance (for instance, the hindered 11-OH group does not react). The CNU acid component can also be esterified directly with the steroid alcohol, using condensation agents such as dicyclohexylcarbodiimide. These reactions can be performed either with or without acylation catalysts such as 4-dimethylaminopyridine. If several OH groups are contained in the steroid, then the most reactive of them preferably react. This type of compound can also be prepared by beginning with a steroid amino acid ester and appending to it the CNU function, for instance by means of conversion with N-(2-ethyl chloride) N-nitroso-carbamoyl azide. Finally, this steroid amino acid ester can also be converted into the desired product with CNU amino acids or CNU di-, tri- or oligopeptides (up to pentapeptides) with the aid of mild condensation reagents such as dicyclohexylcarbodiimide.

The reactions can be illustrated as follows:

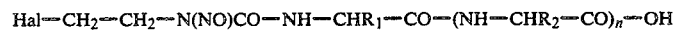  A.

↓ activation

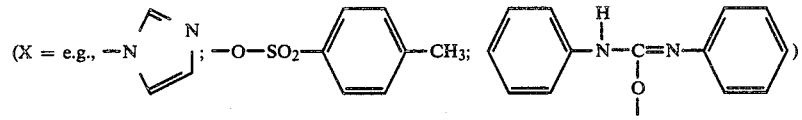

↓ + steroid—OH
  − HX

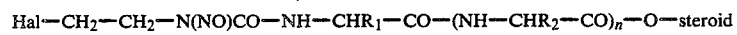

$R_1$, $R_2$, n and Hal have the same meanings here and in models B and C as in claim 1. X is a reactive monovalent group.

Steroid—O—(CO—CHR$_2$—NH)$_n$—CO—CHR$_1$—NH$_2$ + X—CO—N(NO)—CH$_2$—CH$_2$—Hal    B.

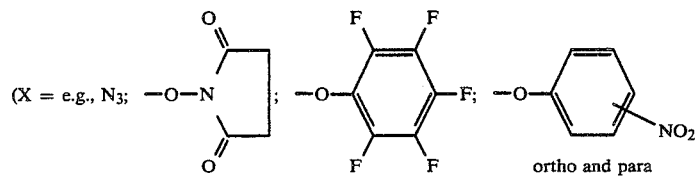

↓ − HX

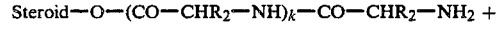    C.

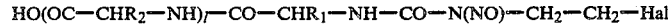

↓ Dicyclohexylcarbodiimide

with k = 0–3
    l = 0–4
    n = 0–5.

The radicals $R_1$ and $R_2$ are radicals of amino acids beyond the carbon atom in the beta position. In the case of aminoacetic acid, this carbon atom is missing, so that these radicals then mean hydrogen. The following can be named as further radicals:

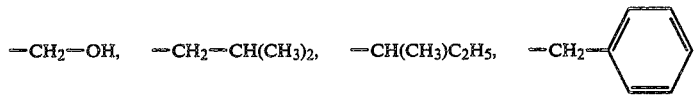

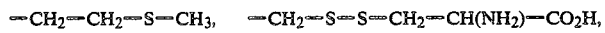

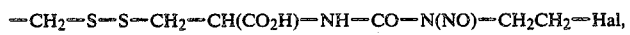

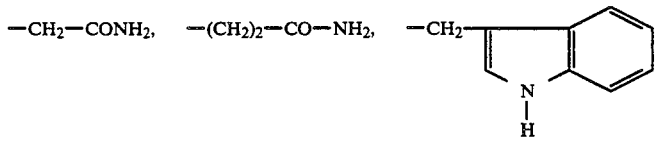

$R_1$ and $R_2$ may be the same or different; if $n>1$, the radicals $R_2$ may also be identical or different among each other.

$R_3$ stands for the radical of a steroid, in particular steroids which can be assigned to the classes of the androgens, estrogens, gestagens and corticosteroids; however, it can also stand for the radical of a stilbene derivative having a pharmacologically similar action, such as diethylstilbestrol.

The symbol Hal here stands for fluorine or chlorine.

In the variant method B, the reactive group X may be, in particular, $N_3$, $O—C_6F_5$,

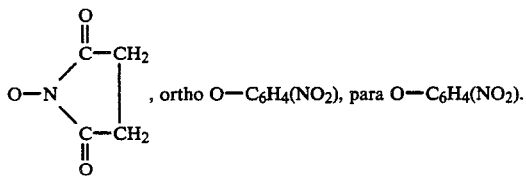

, ortho $O—C_6H_4(NO_2)$, para $O—C_6H_4(NO_2)$.

In the method variant, dicyclohexylcarbodiimide is preferred as the condensation agent. The alternative possibility also exists here of performing a conversion in the aqueous system, using water-soluble carbodiimides, such as 1-cyclohexyl-3-(2-morpholino-ethyl)-carbodiimide-metho-4-toluolsulfonate or 1-ethyl-3-(3-dimethylaminopropyl)-carbodiimide hydrochloride. In the case of water-soluble carbodiimides, it is thus also possible to use aqueous solvent systems.

The following examples explain the invention:

EXAMPLE 1

N-(2-chloroethyl)-N-nitroso-carbamoyl-L-alanine-cortisone-21-ester a. 1.7 g of N,N-carbonyldiimidazole are mixed in 50 ml of absolute tetrahydrofurane (THF) with 2.3 g of CNU-L-alanine; with intensive gas generation, the desired imidazolide is produced. To attain complete conversion, the mixture is stirred 1 h at room temperature (RT). Then 3.6 g of cortisone is added and the mixture stirred 6 h at RT. The THF is then removed by the rotary evaporator and the residue absorbed in 500 ml of acetic ester. Extraction by shaking with ice water, ice-cold NaHCO$_3$ solution, ice-cold NaHSO$_4$ solution, ice water and saturated NaCl solution is performed, and the yellow acetic ester extract is dried over Na$_2$SO$_4$.

After chromatography over silica gel, 4.2 g (75%) of n-(2-ethyl chloride)-N-nitroso-carbamoyl-L-alanine-cortisone-21-ester are obtained. Recrystallization by absorption in dichloromethane or acetic ester and the slow addition of n-pentane with subsequent chilling in the deep-freezer produces light yellow crystals.

F.p.: 169° C. (decomposition!)

Quantitative analysis: Calculated: C 57.29; H 6.41; Cl 6.26; N 7.42. Ascertained: C 57.43; H 6.62; Cl 6.20; N 7.32.

The $^{13}$C NMR spectrum is in agreement with the structure indicated.

The following preparations were also made:

b. N-(2-chloroethyl)-N-nitroso-carbamoyl-L-alanine-pregnenolone-ester. Yield: 50% Light yellow crystals, f.p. 158° C. (decomposition) (from dichloromethane/n-pentane as in Example 1a). Quantitative analysis: Calculated: C 62.12; H 7.72; Cl 6.79; N 8.05. Ascertained: C 61.94; H 7.98; Cl 7.00; [N] 7.98.

c. N-(2-chloroethyl)-N-nitroso-carbamoyl-L-alanine-estrone-ester, yield: 60%

Light yellow crystals, f.p.: 158° C. (decomposition) (recrystallization as in Example 1a).

Quantitative analysis: Calculated: C 60.56; H 6.35; N 8.83; Cl 7.45. Ascertained: C 60.76; H 6.58; N 8.63; Cl 7.59.

d. N-(2-chloroethyl)-N-nitroso-carbamoyl-L-alanine-estradiol-3-ester, yield: 60%

Light yellow crystals, f.p.: 140° C. (decomposition) (recrystallization as in Example 1a).

Quantitative analysis: Calculated: C 60.31; H 6.75; Cl 7.42; N 8.79. Ascertained: C 60.42; H 7.05; Cl 7.50; N 9.03.

The $^{13}$C NMR spectrum is in agreement with the structure indicated.

e. N-(2-chloroethyl)-N-nitroso-carbamoyl-L-alanine-prednisolone-21-ester, yield: 70%

Light yellow crystals, f.p. 168° C. (decomposition) after absorption in THF, addition of acetic acid and chilling.

Quantitative analysis: Calculated: C 57.29; H 6.41; N 7.42. Ascertained: C 57.07; H 6.51; N 7,38; Cl 6.35.

The $^{13}$C NMR spectrum is in agreement with the structure indicated.

f. N-(2-chloroethyl)-N-nitroso-carbamoyl-L-alanine-cis-androsterone-ester, yield 60%, light yellow needles, f.p.: 114° C. (decomposition).

Quantitative analysis: Calculated: C 60.53; H 7.72; Cl 7.15; N 8.47. Ascertained: C 60.78; H 7.91; Cl 6.98; N 8.50.

The $^{13}$C NMR spectrum confirms the structure indicated.

g. N-(2-chloroethyl)-N-nitroso-carbamoyl-L-alanine-desoxy-corticosterone-ester, yield 70%

Light yellow needles, f.p.: 107° C. (decomposition).

Quantitative analysis: Calculated: C 60.50; H 7.15; Cl 6.61; N 7.84. Ascertained: C 60.52; H 7.05; Cl 6.81; N 8.05.

h. N-(2-chloroethyl)-N-nitroso-carbamoyl-L-alanine-dihydrotestosterone-17β-ester Yield: 70%, f.p.: 130° C. (decomposition), light yellow needles, quantitative analysis: Calculated: C 60.53; H 7.72; Cl 7.15; N 8.47. Ascertained: C 60.67; H 7.82; Cl 7.32; N 8.39.

i. N-(2-chloroethyl)-N-nitroso-carbamoyl-L-alanyl-L-alanine-prednisolone-21-ester, Light yellow crystals, yield: 50%. F.p.: 130° C.

Quantitative analysis: Calculated: C 56.56; H 6.49; N 8.79. Ascertained: C 56.26; H 7.12; N 8.41.

Analogously to the above examples, instead of the steroid alcohol a stilbene derivative with a phenolic OH group can be converted.

If CNU alanine/coupling reagent is used in excess, then with diethylstilbestrol the diester is produced; with CNU alanine/coupling reagent in deficit, then with diethylstilbestrol the monoester is favored.

k. N-(2-chloroethyl)-N-nitroso-carbamoyl-L-alaine-diethylstilbestrol-diester

Yield: 70%, light yellow crystals, f.p.: 102° C. (decomposition).

Quantitative analysis: Calculated: C 53.02; H 5.34; Cl 10.43; N 12.37. Ascertained: C 52.98; H 5.05; Cl 10.35; N 12.08.

l. N-(2-chloroethyl)-N-nitroso-carbamoyl-L-alanine-diethylstilbestrol-monoester

Yield: 50%, light yellow crystals, f.p.: 122° C.

Quantitative analysis: Calculated: C 60.82; H 5.98; Cl 7.48; N 8.87. Ascertained: C 60.60; H 6.10; Cl 7.31; N 9.04.

EXAMPLE 2

N-(2-chloroethyl)-N-nitroso-carbamoyl-L-alanine-cortisone-21-ester 1.2 g of CNU alanine are dissolved in 50 ml of pyridine. At 0° C., 1 g of p-toluolsulfonylchloride is added. The mixture is stirred for 15 min at 0° C. and then 1.8 g of cortisone are added. Stirring is performed for 2 h at 0° C. and then a further 5 h at RT. Then the reaction mixture is poured onto ca. 1 l of ice water. The precipitate is vacuum filtered, absorbed in 200 ml of acetic ester and extracted by shaking with ice-cold $NaHSO_4$ solution; ice water; ice-cold $NaHCO_3$ solution; ice water and finally with saturated saline solution, dried over $Na_2SO_4$ and chromatographed over silica gel.

Yield: 50%.

EXAMPLE 3

N-(2-chloroethyl)N-nitroso-carbamoyl-L-alanine-estrone-ester 1.2 g of CNU alanine are dissolved in 30 ml of absolute tetrahydrofurane. At 0° C., 1.1 g of dicyclohexyl-carbodiimide are added. After approximately 5 min, severe turbulence sets in, and a white precipitate forms. After 2 h at 0° C., stirring is performed for 5 h at RT and the precipitate is then filtered off. The filtrate is condensed in the rotary evaporator and absorbed in 200 ml of acetic ester and extracted by shaking with ice-cold $NaCHO_3$ solution, ice water and saturated saline solution. After drying over $Na_2SO_4$, chromatography is performed over silica gel.

Yield: 50%.

Data on the toxicity of the compounds

N-2-chloroethyl)-N-nitroso-carbamoyl-L-alanine-cortisone-21-ester $LD_{50}$: 220–280 mg/kg, period of observation: 90 days.

$LD_{50}$ of CNU alanine: 40–50 mg/kg

This example shows that the linking of CNU alanine with cortisone brings about a sharp reduction in toxicity (by approximately threefold).

In the therapy test using the model of rat leukemia L 5222 (Ivankovic, Zeller, Leukämie L 5222 des Rattenstammes BD IX. Eine durch Äthylnitrosoharnstoff induzierte monozytär-myeloische, transplantierbare Form für zytochemische und chemotherapeutische Studien [Leukemia L 5222 of Rats of Stock BD IX. A monocytic-myeloid, transplantable form induced by ethylnitrosourea for cytochemical and chemotherapeutic studies]. Blut [Blood], 28; 288–292, 1974 and Zeller, Ivankovic, Schmähl, Cancer Research, Vol. 35, 1168–1174, 1975), the cortisone conjugate has good activity. At 176 mg/kg, the total median (replicated experiment!) at 65 days was 3 cured animals out of 6, while with CNU alanine in an equimolar dose with cortisone no cures were attained, with a median survival time of 20 days.

With N-(2-chloroethyl)-N-nitroso-carbamoyl-L-alanine-estrone-ester, the optimal dose was previously 351 mg/kg. The total median in L 5222 here is 43 days. This means that the toxicity (measured in tumor-bearing animals!) is even lower than with the cortisone derivative.

With N-(2-chloroethyl)-N-nitroso-carbamoyl-L-alanine-estradiol-3-ester, the optimal dose was previously 279 mg/kg with a median survival time of 49 days with 2 cures. The estrogen-linked compounds were subjected to an estrogen receptor test (Lebercytosol) (Kranzfelder, Schneider, von Angerer, Schöneberger, J. Cancer Research Chim. Oncol. 97, 167–186 (1980)). The result for the estrone derivative was an affinity of 4% that of the estradiol (100%) for the parameter of 50% bonding inhibition of the $^3H$-tagged estradiol used and an affinity of 16% with the estradiol derivative (at respective amounts of 190 and 50 mmol).

We claim:

1. A method for preparing N-(2-Hal-ethyl)-N-nitroso-carbamoyl-amino acid steroid esters having the structure:

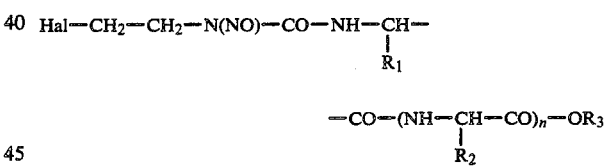

wherein $R_1$ and $R_2$, which may be identical or different, signify the radical of an amino acid from the carbon atom in the beta position or H;

$R_3$ signifies the esterified radical of a steroid, having an esterifiable OH group at the 3, 17 or 21 position attached to the steroid skeleton thereof, of the estrane, androstane or pregnane series or a corticostoid, or of a stilbene derivative having at least one esterifiable OH group without steric hindrance and selected from:

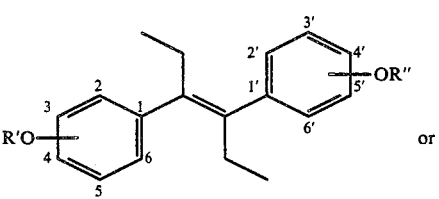

or

-continued

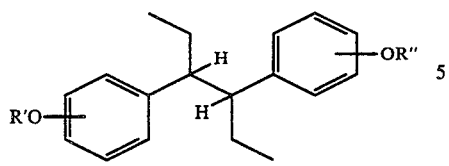

with R' =

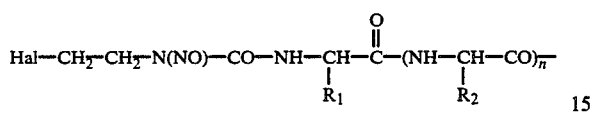

and

R" is H, R, lower alkyl, acetyl or benzoyl;

n is 0 to 5; and Hal is chlorine or fluorine, said $R_3$ radical having a free reactive site which binds itself selectively to a receptor site on a neoplastic cell wherein N-(2-Hal-ethyl)-N-nitrosocarbamoyl-amino acids or N-(2-Hal-ethyl)-N-nitrosocarbomoyl-di-, tri- or oligopeptides, up to hexapeptides, are converted in a solvent with cooperation of an activation or condensation agent selected from the group consisting of N,N'-carbonyl-diimidazole, dicychlohexylcarbodiimide and p-toluolsulfonylchloride/tertiary amine, with steroid alcohols or stilbene derivatives corresponding to the corresponding said steroid esters.

2. A method for preparing N-(2-Hal-ethyl)-N-nitrosocarbamoyl-amino acid steroid esters having the structure:

Hal—CH$_2$—CH$_2$—N(NO)—CO—NH—CH—
$\quad\quad\quad\quad\quad\quad\quad\quad\quad\quad\quad\quad\quad$ | 
$\quad\quad\quad\quad\quad\quad\quad\quad\quad\quad\quad\quad\quad$ R$_1$ —CO—(NH—CH—CO)$_n$—OR$_3$
$\quad\quad\quad\quad$ |
$\quad\quad\quad\quad$ R$_2$ wherein R$_1$ and R$_2$, which may be identical or different, signify the radical of an amino acid from the carbon atom in the beta position or H;

R$_3$ signifies the esterified radical of a steroid, having an esterifiable OH group at the 3, 17 or 21 position attached to the steroid skeleton thereof, of the estrane, androstane or pregnane series or a corticostoid, or of a stilbene derivative having at least one esterifiable OH group without steric hindrance and selected from:

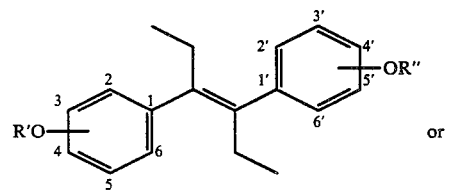

or

-continued

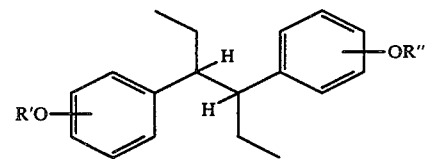

with R' =

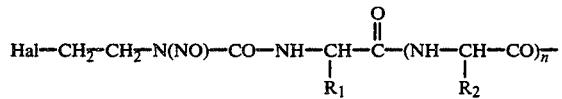

and

R" is H, R, lower alkyl, acetyl or benzoyl;

n is 0 to 5; and Hal is chlorine or fluorine, said $R_3$ radical having a free reactive site which binds itself selectively to a receptor site on a neoplastic cell, wherein corresponding steroid amino acid esters or steroid di-, tri- or oligopeptide esters, up to hexapeptides, of the corresponding said steroids or the corresponding said stilbene derivatives are converted with N-(2-Hal-ethyl)-N-nitroso-carbamoylation agents of the formula Hal—CH$_2$—CH$_2$—N(NO)CO—X, wherein X stands for a reactive group, in a solvent.

3. A method for preparing N-(2-Hal-ethyl)-N-nitrosocarbamoyl-peptide esters of steroids having the structure:

Hal—CH$_2$—CH$_2$—N(NO)—CO—NH—CH—
$\quad\quad\quad\quad\quad\quad\quad\quad\quad\quad\quad\quad\quad$ |
$\quad\quad\quad\quad\quad\quad\quad\quad\quad\quad\quad\quad\quad$ R$_1$ —CO—(NH—CH—CO)$_n$—OR$_3$
$\quad\quad\quad\quad$ |
$\quad\quad\quad\quad$ R$_2$ wherein R$_1$ and R$_2$, which may be identical or different, signify the radical of an amino acid from the carbon atom in the beta position or H;

R$_3$ signifies the esterified radical of a steroid, having an esterifiable OH group at the 3, 17 or 21 position attached to the steroid skeleton thereof, of the estrane, androstane or pregnane series or a corticostoid, or of a stilbene derivative having at least one esterifiable OH group without steric hindrance and selected from:

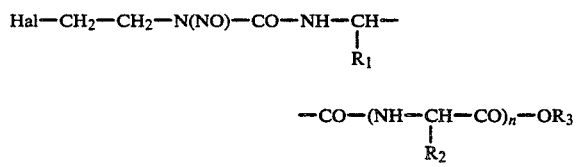

or

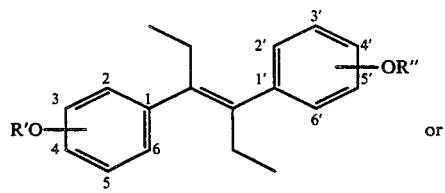

with R' =

-continued

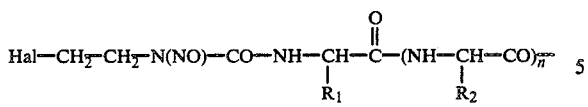

and
R" is H, R, lower alkyl, acetyl or benzoyl;
n is 0 to 5; and Hal is chlorine or fluorine, said $R_3$ radical having a free reactive site which binds itself selectively to a receptor site on a neoplastic cell, wherein corresponding steroid amino acid esters or the corresponding stilbene derivatives were converted with N-(2-Hal-ethyl)-N-nitrosocarbamoyl amino acids or N-(2-Hal-ethyl)-N-nitrosocarbamyl-di-, tri- and oligopeptides, up to pentapeptides, in a solvent with the cooperation of a condensation agent selected from the group consisting of N,N'-carbonyldiimidazole, dicyclohexylcarbodiimide and p-toluolsulfonylchloride/tertiary amine.

4. A method as defined by claim 1, wherein the conversion of the components takes place with the additional cooperation of acylation catalysts selected from the group consisting of 4-dimethylaminopyridine, 4-pyrrolidino-pyridine and 1-hydroxybenzotriazole.

5. A method as defined by claim 1, wherein the conversion takes place in tetrahydrofurane, $CH_2Cl_2$, $CHCl_3$, benzene, toluol or pyridine.

6. A method as defined by claim 1, wherein the conversion of the components is performed in a temperature range from $-10°$ C. up to the boiling point of the solvent, but at a maximum up to the temperature of decomposition of the desired reaction product or of the reaction partners.

7. A method as defined by claim 2, wherein the conversion of the components takes place with the additional cooperation of acylation catalysts selected from the group consisting of 4-dimethylaminopyridine, 4-pyrrolidino-pyridine and 1-hydroxybenzotriazole.

8. A method as defined by claim 2, wherein the conversion takes place in tetrahydrofurane, $CH_2Cl_2$, $CHCl_3$, benzene, toluol or pyridine.

9. A method as defined by claim 2, wherein the conversion of the components is performed in a temperature range from $-10°$ C. up to the boiling point of the solvent, but at a maximum up to the temperature of decomposition of the desired reaction product or of the reaction partners.

10. A method as defined by claim 3, wherein the conversion of the components takes place with the additional cooperation of acylation catalysts selected from the group consisting of 4-dimethylamino-pyridine, 4-pyrrolidino-pyridine and 1-hydroxybenzotriazole.

11. A method as defined by claim 3, wherein the conversion takes place in tetrahydrofurane, $CH_2Cl_2$, $CHCl_3$, benzene, toluol or pyridine.

12. A method as defined by claim 3, wherein the conversion of the components is performed in a temperature range from $-10°$ C. up to the boiling point of the solvent, but at a maximum up to the temperature of decomposition of the desired reaction product or of the reaction partners.

13. Steroid-N-(2-halogenethyl)-N-nitroso-carbamoyl-amino acid or peptide ester of the general formula:

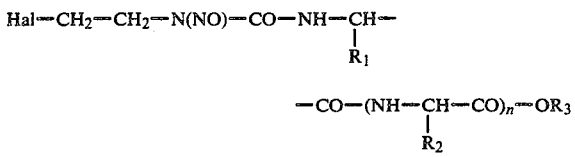

wherein
$R_1$ and $R_2$, which may be identical or different, signify the radical of an amino acid from the carbon atom in the beta position or H;
$R_3$ signifies the esterified radical of a steroid, having an esterifiable OH group at the 3, 17 or 21 position attached to the steroid skeleton thereof, of the estrane, androstane or pregnane series or a corticostoid, or of a stilbene derivative having at least one esterifiable OH group without steric hindrance and selected from:

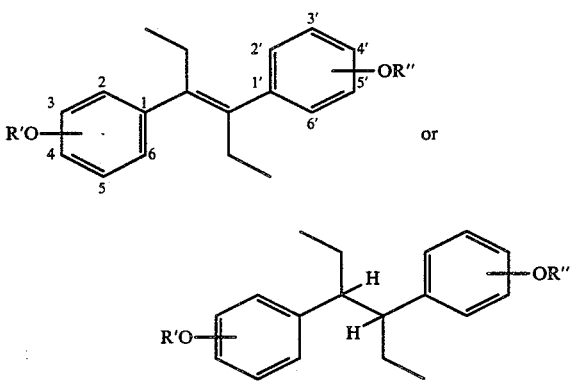

with R' =

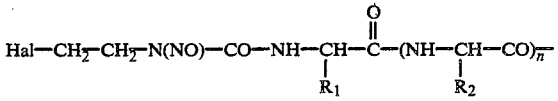

and
R" is H, R, lower alkyl, acetyl or benzoyl;
n is 0 to 5; and Hal is chlorine or fluorine, said $R_3$ radical having a free reactive site which binds itself selectively to a receptor site on a neoplastic cell.

14. Steroid-N-(2-halogenethyl)-N-nitroso-carbamoyl-amino acid or peptide ester according to claim 13 selected from the group consisting of N-(2-chloroethyl)-N-nitroso-carbamoyl-L-alanine-cortisone-21-ester; N-(2-chloroethyl)-N-nitroso-carbamoyl-L-alanine-pregnenolone-ester; N-(2-chloroethyl)-N-nitroso-carbamoyl-L-alanine-estrone-ester; N-(2-chloroethyl)-N-nitroso-carbamoyl-L-alanine-estradiol-3-ester; N-(2-chloroethyl)-N-nitroso-carbamoyl-L-alanine-prednisolone-21-ester; N-(2-chloroethyl)-N-nitroso-carbamoyl-L-alanine-cis-androsteroneester; N-(2-chloroethyl)-N-nitrosocarbamoyl-L-alanine-desoxy-corticosterone-ester; N-(2-chloroethyl)-N-nitroso-carbamoyl-L-alanine-dihydrotestosterone-17β-ester; N-(2-chloroethyl)-N-nitroso-carbamoyl-L-alanyl-L-alanine-prednisolone-21-ester; N-(2-chloroethyl)-N-nitrosocarbamoyl-L-alanine-diethylstilbestrol-diester; and N-(2-chloroethyl)-N-nitroso-carbamoyl-L-alanine-diethylstilbestrolmonoester.

15. The ester of claim 13 wherein said steroid is a member of the estrane series.

* * * * *